(12) United States Patent
Kassab et al.

(10) Patent No.: US 8,876,690 B2
(45) Date of Patent: Nov. 4, 2014

(54) DEVICES, SYSTEMS, AND METHODS FOR DEFORMING A BODY CHANNEL

(75) Inventors: Ghassan S. Kassab, Zionsville, IN (US); Jose A. Navia, Sr., Buenos Alres (AG)

(73) Assignee: CVDevices, LLC, San Diego, CA (US)

( * ) Notice: Subject to any disclaimer, the term of this patent is extended or adjusted under 35 U.S.C. 154(b) by 1262 days.

(21) Appl. No.: 12/602,346

(22) PCT Filed: May 29, 2008

(86) PCT No.: PCT/US2008/065099
§ 371 (c)(1),
(2), (4) Date: Nov. 30, 2009

(87) PCT Pub. No.: WO2008/150878
PCT Pub. Date: Dec. 11, 2008

(65) Prior Publication Data
US 2010/0179376 A1      Jul. 15, 2010

Related U.S. Application Data

(60) Provisional application No. 60/940,604, filed on May 29, 2007.

(51) Int. Cl.
*A61F 2/00* (2006.01)

(52) U.S. Cl.
CPC .................................. *A61F 2/0018* (2013.01)
USPC ....................................................... 600/29

(58) Field of Classification Search
USPC ............... 600/29, 30, 37, 9, 12, 15; 606/151; 128/897–899; 63/3, 6, 15.1, 15.7, 900
See application file for complete search history.

(56) References Cited

U.S. PATENT DOCUMENTS

| 3,815,576 A | 6/1974 | Balaban |
| 3,926,175 A | 12/1975 | Allen et al. |
| 4,053,952 A | 10/1977 | Goldstein |
| 4,551,862 A | 11/1985 | Haber |
| 4,643,169 A | 2/1987 | Koss et al. |
| 4,705,518 A | 11/1987 | Baker et al. |
| 4,994,019 A | 2/1991 | Fernandez et al. |

(Continued)

FOREIGN PATENT DOCUMENTS

| WO | WO2004037134 | 5/2004 |
| WO | WO2008005385 | 1/2008 |
| WO | WO2008091614 | 7/2008 |

OTHER PUBLICATIONS

International Searching Authority, International Search Report, mailed Oct. 1, 2008 (PCT/US08/65099).

(Continued)

*Primary Examiner* — Charles A Marmor, II
*Assistant Examiner* — Shannon McBride
(74) *Attorney, Agent, or Firm* — Reichel IP LLP; Mark C. Reichel; Natalie J. Dean

(57) ABSTRACT

Devices, system and methods for deforming body channels are disclosed herein. At least some embodiments described may be used to deform a body channel so as to decrease or prevent the normal intrachannel flow of material within the body channel. Such deformation may be used to treat such maladies as Gastroesophageal Reflux Disease.

32 Claims, 11 Drawing Sheets

(56) References Cited

U.S. PATENT DOCUMENTS

| | | | |
|---|---|---|---|
| 5,509,888 A * | 4/1996 | Miller | 600/29 |
| 5,572,887 A * | 11/1996 | Geswelli | 63/3 |
| 6,086,525 A | 7/2000 | Davey et al. | |
| 6,097,984 A | 8/2000 | Douglas | |
| 6,135,945 A | 10/2000 | Sultan | |
| 6,293,923 B1 * | 9/2001 | Yachia et al. | 604/96.01 |
| 6,319,191 B1 | 11/2001 | Sayet et al. | |
| 6,409,656 B1 | 6/2002 | Sangouard et al. | |
| 6,647,746 B2 * | 11/2003 | Bosque et al. | 63/3 |
| 6,709,385 B2 | 3/2004 | Forsell | |
| 6,736,823 B2 * | 5/2004 | Darois et al. | 606/151 |
| 6,997,952 B2 | 2/2006 | Furukawa et al. | |
| 7,013,674 B2 * | 3/2006 | Kretchmer | 63/5.1 |
| 7,175,589 B2 | 2/2007 | Deem et al. | |
| 7,201,757 B2 | 4/2007 | Knudson et al. | |
| 7,223,228 B2 | 5/2007 | Timm et al. | |
| 7,937,965 B2 * | 5/2011 | Hering | 63/15.1 |
| 8,113,013 B2 * | 2/2012 | Kessler | 63/40 |
| 2004/0122470 A1 * | 6/2004 | Deem et al. | 606/213 |
| 2004/0242956 A1 | 12/2004 | Scorvo | |
| 2005/0075530 A1 * | 4/2005 | Kaizuka | 600/9 |
| 2006/0009674 A1 * | 1/2006 | Miller | 600/30 |
| 2006/0129022 A1 * | 6/2006 | Venza et al. | 600/13 |
| 2006/0252982 A1 | 11/2006 | Hassler, Jr. et al. | |
| 2006/0252983 A1 * | 11/2006 | Lembo et al. | 600/37 |
| 2007/0038015 A1 * | 2/2007 | Quail | 600/9 |
| 2007/0073098 A1 | 3/2007 | Lenker et al. | |

OTHER PUBLICATIONS

International Searching Authority, Written Opinion of the International Searching Authority, mailed Oct. 1, 2008 (PCT/US08/65099).

* cited by examiner

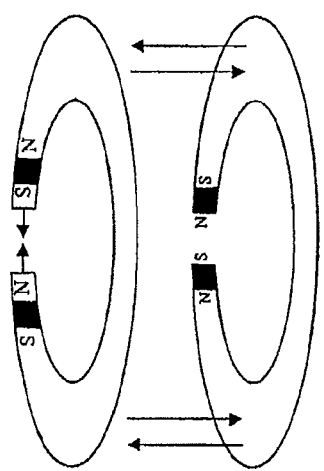
Figure 1 (Previous Disclosure)

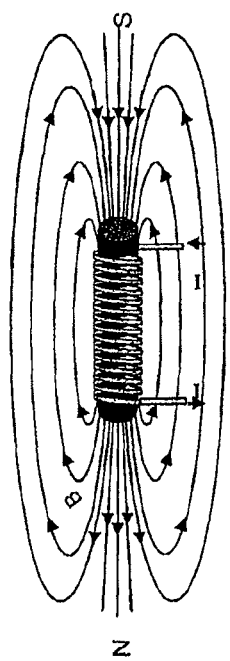
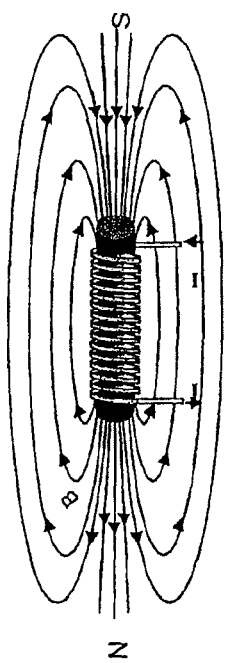
Figure 2 (Previous Disclosure)

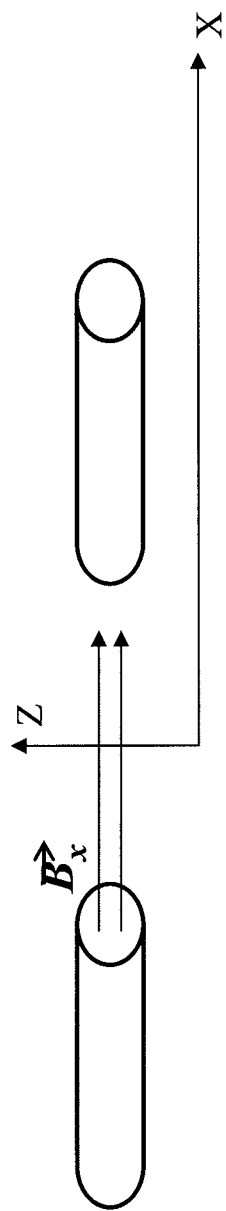
Figure 3 (Previous Disclosure)

US 8,876,690 B2

DEVICES, SYSTEMS, AND METHODS FOR DEFORMING A BODY CHANNEL

PRIORITY

The present application is related to, and claims the priority benefit of, International Patent Application Serial No. PCT/US2008/065099, filed May 29, 2008, which is related to, and claims the priority benefit of, U.S. Provisional Patent Application Ser. No. 60/940,604, filed May 29, 2007. The contents of each of these applications are hereby incorporated by reference in their entirety into this disclosure.

BACKGROUND

Acid Reflux

Gastroesophageal Reflux Disease (GERD) is defined as symptoms of mucosal damage produced by the abnormal reflux of gastric contents into the esophagus. GERD is a condition in which the acidified liquid content of the stomach backs up into the esophagus. The causes of GERD comprise an abnormal lower esophageal sphincter, hiatal hernia, abnormal esophageal contractions, and slow emptying of the stomach.

Approximately 4.6 to 18.6 million people in the United States have GERD. GERD can have a significant impact on quality of life. GERD can be classified in two ways: uncomplicated GERD or complicated GERD. The symptoms of uncomplicated GERD are heartburn, regurgitation, and nausea. Complications of GERD include ulcers and strictures of the esophagus, Barrett's esophagus, cough and asthma, throat and laryngeal inflammation, inflammation and infection of the lungs, and collection of fluid in the sinuses and middle ear. Barrett's esophagus is a pre-cancerous condition that requires periodic endoscopic surveillance for the development of cancer. GERD is treated with life-style changes, antacids, histamine antagonists (H2 blockers), proton pump inhibitors (PPIs), pro-motility drugs, foam barriers, surgery, and endoscopy.

Urinary Incontinence

Urinary incontinence is the inability to control the release of urine from the bladder. The loss of bladder control—known as urinary incontinence—is an all too common, often embarrassing and frustrating problem for millions of people. The five main types of urinary incontinence are stress incontinence, urge incontinence, overflow incontinence, mixed incontinence and functional incontinence. Other types of urinary incontinence include reflex incontinence, total incontinence and nocturnal enuresis.

More often, urinary incontinence is a persistent condition caused by some underlying physical problem such as weakened muscles, nerve problems or an obstruction in the urinary tract. Factors that can lead to chronic incontinence include pregnancy and childbirth, hormonal changes following menopause, hysterectomy, interstitial cystitis, prostatitis, enlarged prostate, prostate cancer, bladder cancer, neurological disorders, obstruction and other illnesses or injuries.

Urinary incontinence can often be corrected with the help of medication but there are frequently side effects. Several medical devices are available to help treat incontinence. Those designed specifically for women include urethral inserts and pessaries. Urethral inserts are small tampon-like disposable devices. Pessaries are small plastic or silicone ring-like devices that are inserted into the vagina to support the bladder.

A common surgical procedure is replacement of the urinary sphincter with an artificial one. The artificial sphincter is a small device and is particularly useful to men who have weakened urinary sphincters from treatment of prostate cancer or an enlarged prostate gland. The procedure is rarely performed on women with stress incontinence. The device is shaped like a doughnut and is implanted around the neck of the bladder. The fluid-filled ring keeps the urinary sphincter shut tight until the patient is ready to urinate. To urinate, the patient presses a valve implanted under the skin that causes the ring to deflate and allows urine in the bladder to be released. This surgery is the most effective procedure for male incontinence. Complications of this procedure is malfunction of the device, which implies a repeat surgery, and infrequent infection.

Fecal Incontinence

Fecal incontinence refers to the involuntary loss of gas or liquid stool (called minor incontinence) or the involuntary loss of solid stool (called major incontinence). Surveys indicate the incidence in the general population to be 2-7 percent, although the true incidence may be much higher because many people are hesitant to discuss this problem with a healthcare provider.

Fecal incontinence can undermine self-confidence, create anxiety, and lead to social isolation. Fecal incontinence is most often caused by injury to one or both of the ring-like muscles, or the nerves that control these muscles, at the end of the rectum called the internal and external anal sphincters. Causes of fecal incontinence can include vaginal childbirth, neurologic disorders, and fecal impaction. In some cases, the cause is unknown. Treatment options for fecal incontinence may include a combination of medication, behavioral changes, stool bulking agents, and surgery.

BRIEF SUMMARY

Various embodiments relate to devices, systems, and methods for deforming a body structure. At least some embodiments may be used to treat a condition associated with a malfunctioning or poorly functioning body structure. An example of one embodiment used to treat a condition is for the treatment of GERD with a poorly functioning lower esophageal sphincter.

According to at least one embodiment of a device for the deformation of a body channel, the device comprises a first rod having a first end, a second end, a first portion extending from the first end to the second end, and a second portion substantially surrounding the first portion, wherein the first end and second end are operable to attract one another, wherein the first portion of the first rod is sufficiently rigid as to exert a force upon a body channel, and wherein the second portion of the first rod comprises a malleable portion sufficient to distribute the force of the first portion exerted upon the body channel. In at least one additional embodiment, the first end and second end display a transient magnetic force, and the first rod is capable of deforming a body channel through the transient magnetic force. In an additional embodiment, the first rod further comprises a first ferromagnetic bar proximate to a first end and a second ferromagnetic bar proximate to the second end, and a first wire having a proximal wire end and a distal wire end, wherein at least a portion of the first wire is in contact with a portion of the first rod, and wherein the first wire is capable of generating a magnetic field. In yet another embodiment, the magnetic field generates a transient magnetic force between the first ferromagnetic bar and the second ferromagnetic bar.

In at least one embodiment of a device for deformation of a body channel, the device further comprises a power source, the power source electrically coupled to the first wire. In at least one embodiment, the power source is operable to provide an electric current to the first wire. In an additional embodiment, the power source comprises a battery. In yet another embodiment, the power source further comprises a control mechanism and a processor operable to process data.

In at least one embodiment of the deformation device, the control mechanism of the deformation device is capable of manual and/or automatic adjustment. In at least one embodiment, the device further comprises a sensor in communication with the power source. The sensor, in at least one embodiment, is operable to detect a predetermined variable. In yet another embodiment, the sensor is operable to detect any one of the deformation of the body channel, the flow of a material within the body channel, a level of pressure exerted by the first rod on the body channel, and temperature. In an additional embodiment, the control mechanism is adjusted automatically through use of the processor by the sensor upon reaching a preset value for the predetermined variable.

In at least one embodiment of the deformation device, the first rod further comprises a joint member, wherein the joint member partitions the first rod into a proximal segment and a distal segment. In at least one embodiment, the joint member allows flexure of the first rod.

In yet another embodiment of the deformation device, the deformation device further comprises a sleeve at least partially sheathing a portion of the first rod. In at least one embodiment, the sleeve may be comprised of any one of silicone, polytetrafluoroethylene, a biological material, small intestinal submucosal material, pericardial tissue. The sleeve, in at least one embodiment, substantially shields exterior surfaces from contact with the electric current.

In at least one embodiment, the deformation device is proximate to the body channel. Further, in an additional embodiment, the device is secured proximate to the body channel by a securing mechanism.

In addition to the two ferromagnetic bars of the embodiment of the deformation device, in at least one embodiment, the first rod further comprises at least one additional ferromagnetic bar located between the first ferromagnetic bar and the second ferromagnetic bar. In an additional embodiment, at least one of the additional ferromagnetic bars is configured to increase a potential deformative force of the first rod. In yet another embodiment, at least one of the ferromagnetic bars comprises neodymium, iron, and boron. Additionally, in at least one embodiment, at least one of the ferromagnetic bars comprises a Heusler alloy or of carbon-coated metal particles. In yet another embodiment, at least one of the ferromagnetic bars consists of a material selected from the group consisting of $Cu_2MnAl$, $Cu_2MnIn$, $Cu_2MnSn$, $Ni_2MnAl$, $Ni_2MnIn$, $Ni_2MnSn$, $Ni_2MnSb$, $Co_2MnAl$, $Co_2MnSi$, $Co_2MnGa$, $Co_2MnGe$, $Pd_2MnAl$, $Pd_2MnIn$, $Pd_2MnSn$, and $Pd_2MnSb$. Further, in at least one embodiment, the first end of the first rod is in proximity to the second end of the first rod, and the first ferromagnetic bar is capable of magnetic attraction to the second ferromagnetic bar.

According to at least one embodiment of a device for the deformation of a body channel, the device comprises a first rod having a first end, a second end, a first portion and a second portion, a second rod having a third end, a fourth end, a third portion and a fourth portion, wherein the first end and the fourth end are operable to attract one another, and the second end and the third end are operable to attract one another, wherein at least two of the first end, the second end, the third end and the fourth end display a transient magnetic force, and the first rod and second rod in conjunction are capable of deforming a body channel through a transient magnetic attractive force. In an additional embodiment, at least one of the first portion and the third portion are sufficiently rigid as to exert a force upon a body channel, and wherein at least one of the second portion and the fourth portion comprise a malleable portion sufficient to distribute the force of the first portion exerted upon the body channel.

According to at least one embodiment of a system for the deformation of a body channel, the system comprises a first rod having a first end, a second end, a first ferromagnetic bar proximate to the first end and a second ferromagnetic bar proximate to the second end, a first wire having a proximal wire end and a distal wire end, wherein at least a portion of the first wire is in contact with a portion of the first rod, a power source operably connected to the first wire, the power source operable to provide an electric current to the first wire, and wherein deliverance of an electric current from the power source to the first wire forms an inductor. In an additional embodiment, the inductor generates a transient magnetic attractive force between the first ferromagnetic bar and the second ferromagnetic bar. In at least one embodiment, the power source comprises a battery. In at least one further embodiment, the power source further comprises a control mechanism and a processor for processing data.

In at least one embodiment of the system for deforming a body channel, the control mechanism of the system is capable of manual and/or automatic adjustment. In at least one embodiment, the system further comprises a sensor in communication with the power source. The sensor, in at least one embodiment, is operable to detect a predetermined variable. In yet another embodiment, the sensor is operable to detect any one of the deformation of the body channel, the flow of a material within the body channel, a level of pressure exerted by the first rod on the body channel, and temperature. In an additional embodiment, the control mechanism is adjusted automatically through use of the processor by the sensor upon reaching a preset value for the predetermined variable.

In at least one embodiment of the system, the first rod further comprises a joint member, wherein the joint member partitions the first rod into a proximal segment and a distal segment. In at least one embodiment, the joint member allows flexure of the first rod.

In yet another embodiment of the system, the system further comprises a sleeve at least partially sheathing a portion of the first rod. In at least one embodiment, the sleeve may be comprised of any one of silicone, polytetrafluoroethylene, a biological material, small intestinal submucosal material, and pericardial tissue. The sleeve, in at least one embodiment, substantially shields exterior surfaces from contact with the electric current.

In at least one embodiment, the system for deforming a body channel is proximate to the body channel. Further, in an additional embodiment, the system is secured proximate to the body channel by a securing mechanism.

In addition to the two ferromagnetic bars of the system, in at least one embodiment, the first rod further comprises at least one additional ferromagnetic bar located between the first ferromagnetic bar and the second ferromagnetic bar. In an additional embodiment, at least one of the additional ferromagnetic bars is configured to increase the potential deformative force of the first rod. In yet another embodiment, at least one of the ferromagnetic bars comprises neodymium, iron, and boron. Additionally, in at least one embodiment, at least one of the ferromagnetic bars comprises a Heusler alloy or carbon-coated metal particles. In yet another embodiment, at least one of the ferromagnetic bars consists of a material selected from the group consisting of $Cu_2MnAl$, $Cu_2MnIn$, $Cu_2MnSn$, $Ni_2MnAl$, $Ni_2MnIn$, $Ni_2MnSn$, $Ni_2MnSb$, $Co_2MnAl$, $Co_2MnSi$, $Co_2MnGa$, $Co_2MnGe$, $Pd_2MnAl$, Pd$_2$MnIn, Pd$_2$MnSn, and Pd$_2$MnSb. Further, in at least one embodiment, the first end of the first rod is in proximity to the second end of the first rod, and the first ferromagnetic bar is capable of magnetic attraction to the second ferromagnetic bar.

According to at least one embodiment of a system for deformation of a body channel, the system further comprises a second rod having a third end, a fourth end, a third ferromagnetic bar proximate to the third end and a fourth ferromagnetic bar proximate to the fourth end, a second wire having a proximal second wire end and a distal second wire end, a portion of the second wire coiled around a portion of the second rod, and a power source operably connected to the second wire, the power source operable to provide an electric current to the second wire, wherein deliverance of an electric current from the power source to the second wire forms an inductor, and wherein the first rod and the second rod are operable for attraction.

According to at least one embodiment of a method for the deformation of a body channel, the method comprises introducing proximate to a body channel a deformation device operable to deform a body channel, wherein the deformation device is operably coupled to a first wire, and wherein the first wire is operably connected to a power source, positioning the deformation device to substantially encircle the body channel, securing the deformation device at a point proximate to the body channel and introducing an electrical current from the power source to the first wire to form an inductor. In an additional embodiment of the method, the device comprises a first rod having a first end, a second end, a first ferromagnetic bar proximate to the first end and a second ferromagnetic bar proximate to the second end. In yet another embodiment of the method, the method further comprises constricting the body channel. Further, in an additional embodiment of the method, the body channel is selected from a group consisting of the: upper esophageal sphincter, lower esophageal (or cardia) sphincter, pyloric sphincter, Illeocecal sphincter, sphincter of Oddi, urethral sphincter, internal anal sphincter, and external anal sphincter. In at least one additional embodiment, the method further comprises introducing a biologically compatible material sheathing the first rod. In an additional embodiment of the method, at least one of the ferromagnetic bars comprises neodymium, iron, and boron. In an additional embodiment, at least one of the ferromagnetic bars comprises a Heusler alloy or carbon-coated metal particles. Further, in at least one additional embodiment, at least one of the ferromagnetic bars consist of a material selected from the group consisting of Cu$_2$MnAl, Cu$_2$MnIn, Cu$_2$MnSn, Ni$_2$MnAl, Ni$_2$MnIn, Ni$_2$MnSn, Ni$_2$MnSb, Co$_2$MnAl, Co$_2$MnSi, Co$_2$MnGa, Co$_2$MnGe, Pd$_2$MnAl, Pd$_2$MnIn, Pd$_2$MnSn, and Pd$_2$MnSb.

In an additional embodiment of the method for deforming a body channel, the method further comprises removing the electrical current from the first wire. Additionally, the method, in at least one embodiment, further comprises introducing a control mechanism. In at least one embodiment, the control mechanism comprises a sensor operably connected to the power source. Further, in at least one embodiment, the control mechanism monitors at least one of: flow, pressure, strain, and deformation of the body channel. Additionally, in at least one embodiment, the control mechanism automatically controls the supply of electrical current to the first rod. The power source, in at least one embodiment of the method, comprises a battery. Additionally, in at least one embodiment, the power source is implanted subcutaneously.

BRIEF DESCRIPTION OF THE DRAWINGS

FIG. 1 shows the magnetic field of two ferromagnetic rods arranged above and below a valve annulus, according to a previous disclosure;

FIG. 2 shows two ferromagnetic rods in the form of magnetic dipoles with electric current being applied, according to a previous disclosure;

FIG. 3 shows a depiction of the computation of horizontal force exerted between two magnets, according to a previous disclosure;

DETAILED DESCRIPTION

Figure 4:
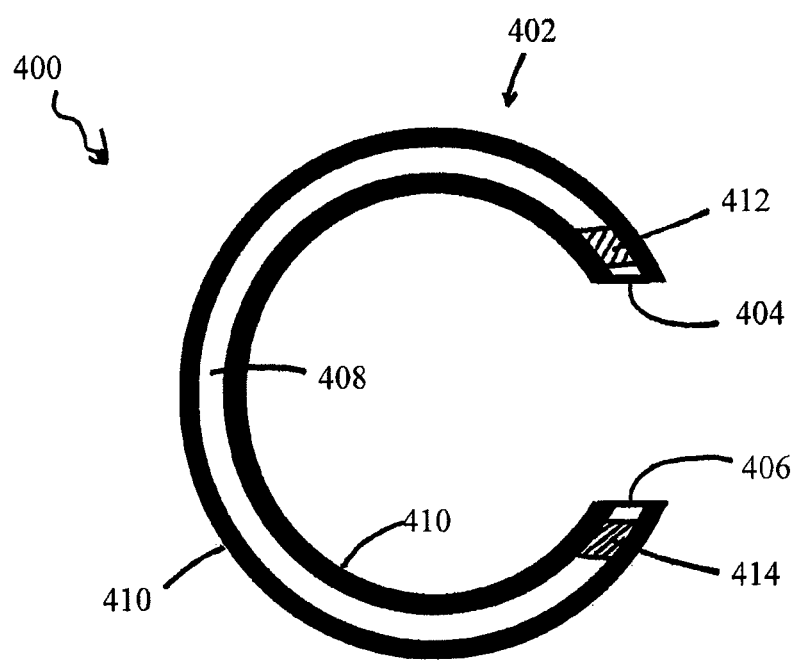
FIG. 4 shows a top view of at least one embodiment of a deformation device of the present disclosure, as described herein.

The present disclosure relates to deformation devices and methods of their use in the deformation of body channels. For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

The disclosed embodiments include devices, systems and methods for the deformation of a body channel. For example, at least some of the embodiments disclosed herein are useful for the deformation of the esophagus, including in some embodiments the lower esophageal sphincter. Such deformation can be used in the treatment of GERD, as referenced herein. Additionally, at least some embodiments disclosed herein are useful for the deformation of the urethra, including in some instances the urinary sphincter, for treatment of urinary incontinence. Further, at least some embodiments disclosed herein are useful for the deformation of the rectum, including in some instances the internal and/or external anal sphincter, for treatment of fecal incontinence.

Previously, the present inventors introduced an invention (U.S. Patent Application No. 60/881,836, later converted to International Application No. PCT/US08/00840) aimed at adjusting or remodeling a valve annulus through electromagnetic force. FIGS. 1-3 show some of the concepts introduced in the prior application, and used in the determination of the motion of the annulus. FIG. 1 shows the magnetic fields generated by two ferromagnetic rods arranged above and below a valve annulus (not shown). In this embodiment, the black squares represent ferromagnetic elements, and the arrows represent the lines of magnetic force.

FIG. 2 shows two ferromagnetic rods in the form of magnetic dipoles, with current applied through lead wires in a coiled arrangement around the ferromagnetic rods to form an inducer. FIG. 3 shows a depiction of how to compute the horizontal force generated between magnets as disclosed in the prior application referenced herein.

FIG. 4 shows a top-down view of at least one embodiment of deformation device for the deformation of a body channel. In the embodiment depicted in FIG. 4, deformation device 400 comprises a first rod 402 having a first end 404 and a second end 406. First rod 402 further comprises a first portion 408 and a second portion 410, wherein first portion 408 is comprised of a material sufficiently rigid as to exert a force upon a body channel, and wherein second portion 410 is comprised of a material sufficiently malleable as to distribute the force of the first portion 408 upon an affected body channel.

First portion 408, may be comprised of any sufficiently rigid material, such as a metal, plastic, composite, or biological material. In at least one embodiment, second portion 410 may be comprised of any one of a silicone material, biological material (SIS, pericardium, etc.), PTFE or other biologically compatible and protective material. In at least one embodiment, second portion 410 may also be comprised of an electrically-protective material.

First end 404 and second end 406 of first rod 402 comprise magnets 412 and 414 respectively, with opposing polarities so that opposing poles of the magnets attract one another. The force of attraction between magnets 412 and 414, in at least this embodiment, may be sufficient to urge first end 404 and second end 406 so as to decrease the distance between the two ends. In at least one embodiment, the magnetic attractive force between magnets 412 and 414 may be of a transient nature. Further, magnets 412 and 414 may be of any size or shape as may be useful exert deformation pressure on a body channel. In at least one embodiment, magnets 412 and 414 may be comprised of any ferromagnetic material known in the art.

Figure 5A:
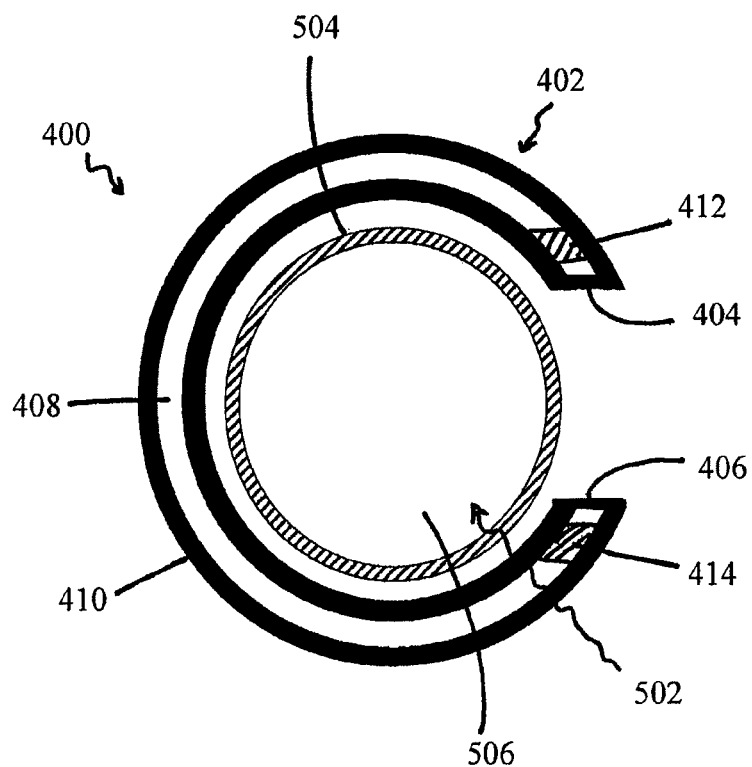
FIG. 5A shows at least one embodiment of a deformation device of FIG. 4 positioned around a body channel, as described herein.

FIG. 5A shows an embodiment of deformation device 400 of FIG. 4 where the deformation device 400 is at least partially surrounding exterior wall 504 of a body channel 502. The body channel 502 further comprises an interchannel space 506. In at least one embodiment, the interchannel space 506 may contain, or allow the passage of, a biological liquid or solid.

Figure 5B:
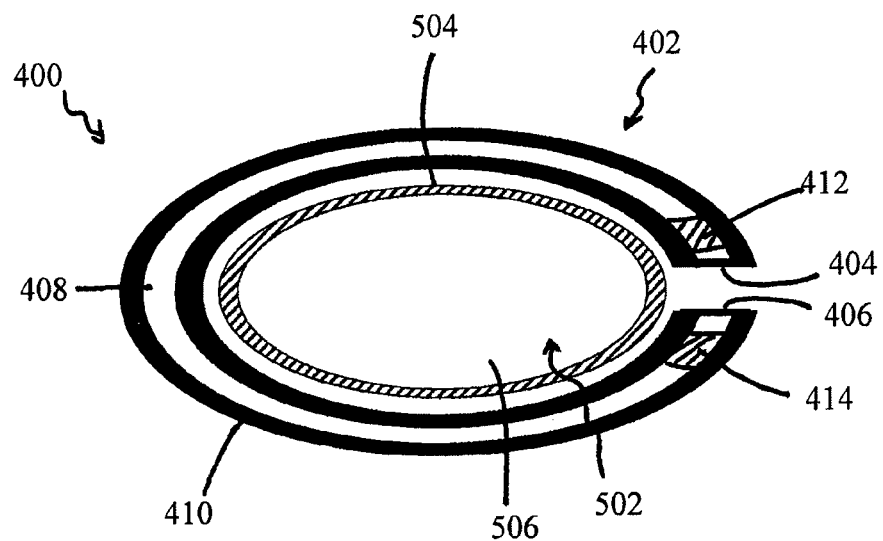
FIG. 5B shows at least one embodiment of a deformation device of FIG. 4 positioned around to a body channel and exerting moderate deformation pressure to the body channel, as described herein.
Figure 5C:
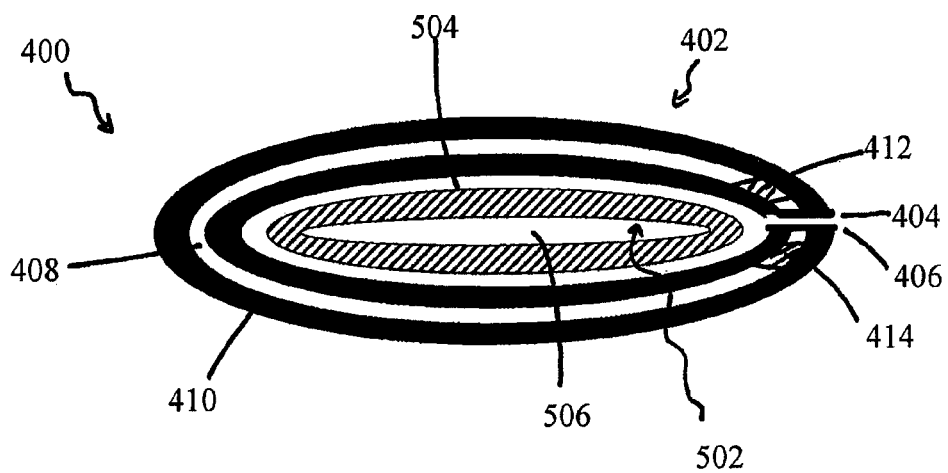
FIG. 5C shows at least one embodiment of a deformation device of FIG. 4 positioned around to a body channel and exerting severe deformation pressure to the body channel, as described herein.

As shown in FIGS. 5B and 5C, as the deformation device 400 begins to exert force upon exterior wall 504, the volume of interchannel space 506 beings to decrease. This decrease in volume may lower the efficiency of passage of a liquid or solid to the point where it is substantially stopped. Compression of the space between the first end 404 and second end 406 of deformation device 400 under moderate magnetic force, as shown in FIG. 5B, passes a significant amount of compressile force onto exterior wall 504 to effect the compression of interchannel space 506. Introduction of severe force upon body channel 502, as depicted in FIG. 5C, produces a significant reduction in volume of interchannel space 506.

Deformation device 400 is sized and shaped in such a manner as to sufficiently encompass the exterior wall 504. In at least one embodiment, the composition of first rod 402 may be of a shape memory alloy or similar material to allow for the shaping of first rod 402 to the surface of the body channel 502.

Figure 6:
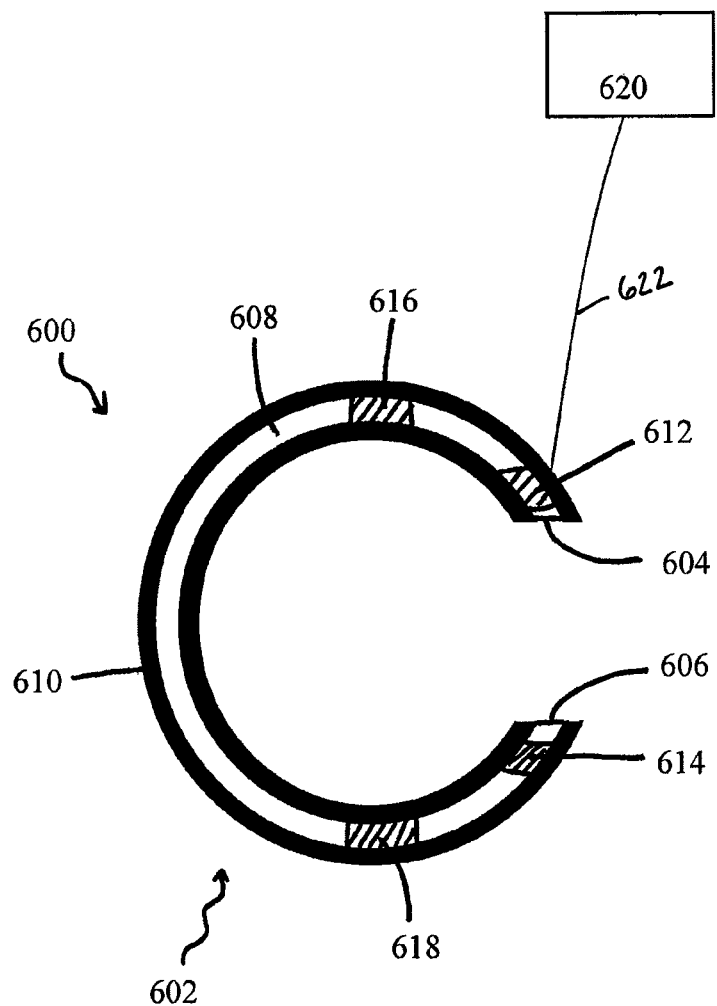
FIG. 6 shows a top view of at least one embodiment of a deformation device, as described herein.

FIG. 6 shows an additional embodiment of a deformation device of the present disclosure. As shown in FIG. 6, an embodiment of deformation device 600 comprising a first rod 602 having a first end 604 and a second end 606 is provided. First rod 602 further comprises a first portion 608 and a second portion 610, wherein first portion 608 is comprised of a material sufficiently rigid as to exert a force upon a body channel, and wherein second portion 610 comprised of a material sufficiently malleable as to distribute the force of first portion 608 upon an affected body channel. First rod 602 further comprises ferromagnetic bars 612 and 614 proximate to first end 604 and second end 606 of first rod 602. Ferromagnetic bars 612 and 614 are in contact with wire 622 electrically coupled to a power supply 620. Upon introduction of an electrical current to wire 622, ferromagnetic bars 612 and 614 display a transient magnetic force towards one another. The device, in some embodiments, may be configured such that when the electric current is turned off the transient magnetic force decreases and/or ceases. Further, in at least one embodiment, the level of magnetic attraction may be adjusted through modification of the level of current applied to wire 622. In at least one embodiment, first rod 602 may further comprise at least one additional ferromagnetic bar between ferromagnetic bars 612 and 614. By way of example, at least one embodiment depicted in FIG. 6 discloses two ferromagnetic bars 616 and 618 between ferromagnetic bars 612 and 614. This depiction is in no way meant to be a limitation on the number or spacing of ferromagnetic bars which may be placed depending on the intended location and usage of deformation device 600.

Figure 7:
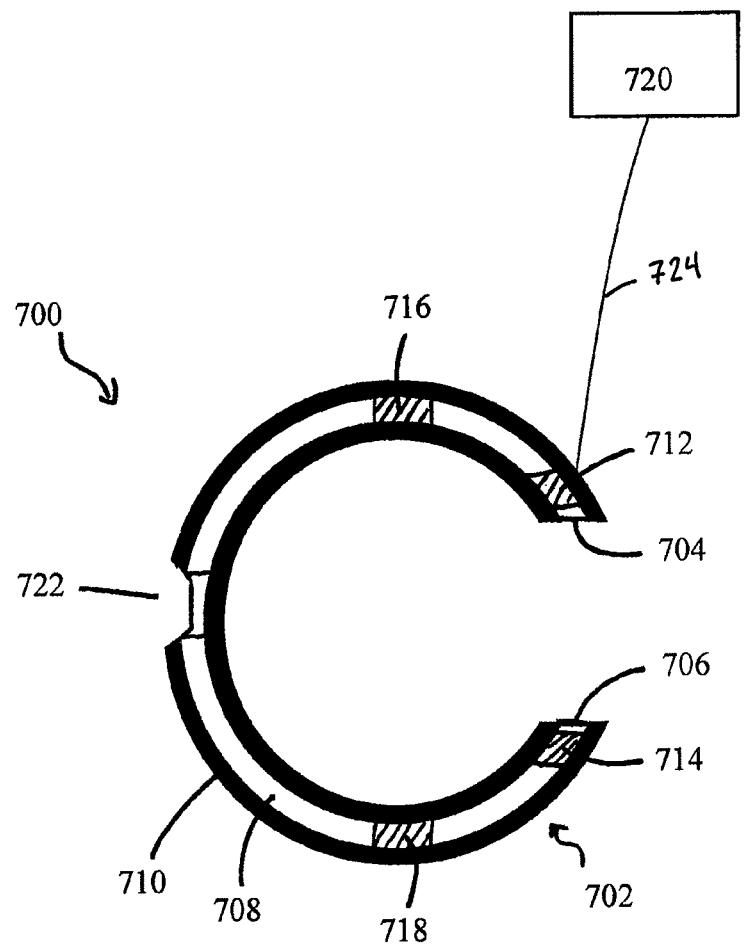
FIG. 7 shows a top view of at least one embodiment of a deformation device, as described herein.

FIG. 7 shows an additional embodiment of a deformation device of the present disclosure. As shown in FIG. 7, an embodiment of deformation device 700 which comprises similar components to deformation device 600 save for the inclusion of joint member 722 is provided. Deformation device 700 comprises first rod 702 having first end 704 and second end 706. First rod 702 further comprises a first portion 708 and a second portion 710, wherein first portion 708 is comprised of a material sufficiently rigid as to exert a force upon a body channel, and wherein second portion 710 is comprised of a material sufficiently malleable as to distribute the force of first portion 708 upon an affected body channel. First rod 702 further comprises ferromagnetic bars 712 and 714 proximate to first end 704 and second end 706, respectively. Ferromagnetic bars 712 and 714 are in contact with wire 724 electrically coupled to a power supply 720. Upon introduction of an electrical current into wire 724, ferromagnetic bars 712 and 714 display a transient magnetic force towards one another. In at least this embodiment, first rod 702 may comprise two additional ferromagnetic bars 716 and 718 between ferromagnetic bars 712 and 714.

Joint member 722 serves to decrease the resistance to flexure of first rod 702 and substantially serves to divide first rod 702 into a proximal and distal region. Inclusion of joint member 722 into deformation device 700 may be dependent upon the site of application and the usage envisioned by the practitioner. For example, the inclusion of joint member 722 may be indicated in an embodiment of first rod 702 comprising a material lacking sufficient flexure to flex in response to the magnetic force generated by the ferromagnetic bars.

Figure 8:
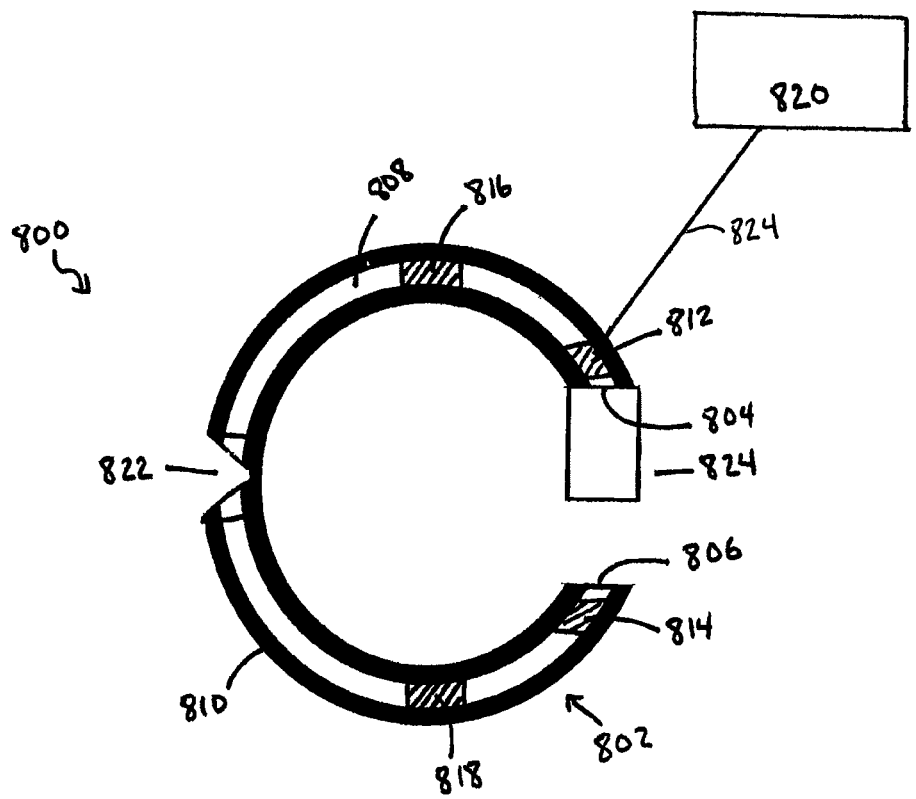
FIG. 8 shows a top view of at least one embodiment of a deformation device, as described herein.

FIG. 8 shows an additional embodiment of a deformation device of the present disclosure. As shown in FIG. 8, an embodiment of deformation device 800 comprising similar components to deformation device 700 save for the inclusion of sleeve 824. Deformation device 800 comprises first rod 802 having first end 804 and second end 806. First rod 802 further comprises first portion 808 and second portion 810, wherein first portion 808 is comprised of a material sufficiently rigid as to exert a force upon a body channel, and wherein second portion 810 is comprised of a material sufficiently malleable as to distribute the force of first portion 808 upon an affected body channel. First rod 802 further comprises ferromagnetic bars 812 and 814 proximate to first end 804 and second end 806, respectively. Ferromagnetic bars 812 and 814 are in contact with wire 824 electrically coupled to power supply 820. Upon introduction of an electrical current into wire 824, ferromagnetic bars 812 and 814 display a transient magnetic force towards one another. In at least this embodiment, first rod 802 may comprise two additional ferromagnetic bars 816 and 818 between ferromagnetic bars 812 and 814.

Joint member 822 serves to decrease the resistance to flexure of first rod 802 and substantially serves to divide first rod 802 into a proximal and distal region. Inclusion of joint member 822 into deformation device 800 may be dependent upon the site of application and the usage envisioned by the practitioner. For example, the inclusion of joint member 822 may be indicated in an embodiment of first rod 802 comprising a material lacking sufficient flexure to flex in response to the magnetic force generated by the ferromagnetic bars.

In at least one embodiment, sleeve 824 is comprised of a biologically compatible material with edges defining an opening at either end. The openings are sufficiently sized and shaped as to removably engage either end 804 or 806 of first rod 802. In at least one embodiment, as depicted in FIG. 8, sleeve 824 is coupled to at least one end of first rod 802. Sleeve 824 at least partially sheaths a portion of first rod 802 from interaction with exterior surfaces.

In at least one embodiment, the biologically compatible material of sleeve 824 may be either silicon or polytetrafluoroethylene. Additionally, in some embodiments sleeve 824 may be comprised of a biological material such as pericardium or submucosal material from the small intestine marketed under the name SIS (Cook Biotech). Further, in at least one embodiment, the biologically compatible material of sleeve 824 is minimally conductive to electric currents.

Figure 9:
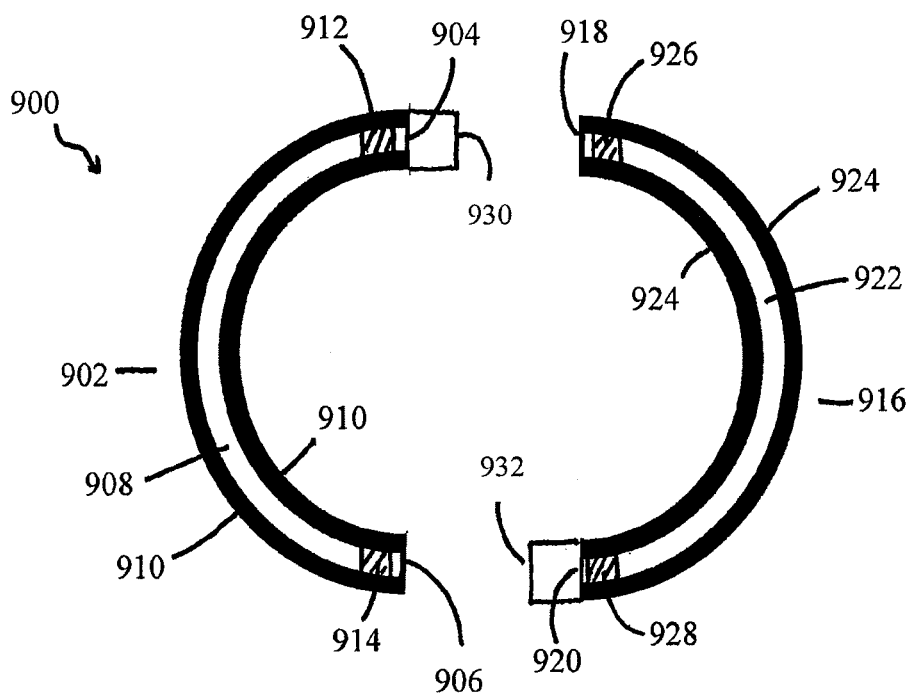
FIG. 9 shows a top view of at least one embodiment of a deformation device, as described herein.

FIG. 9 shows an exemplary embodiment of deformation device 900, where device 900 comprises first rod 902 and second rod 916. First rod 902 comprises first end 904 and second end 906. First rod 902 further comprises first portion 908 and second portion 910, wherein first portion 908 is comprised of a material sufficiently rigid as to exert a force upon a body channel, and wherein second portion 910 is comprised of a material sufficiently malleable as to distribute the force of first portion 908 upon an affected body channel. First rod 902 further comprises ferromagnetic bars 912 and 914 proximate to first end 904 and second end 906, respectively. Second rod 916 comprises a third end 918 and a fourth end 920. Second rod 916 further comprises third portion 922 and fourth portion 924, wherein third portion 922 is comprised of a material sufficiently rigid as to exert a force upon a body channel, and wherein fourth portion 924 is comprised of a material sufficiently malleable as to distribute the force of third 922 upon an affected body channel. Second rod 916 further comprises ferromagnetic bars 926 and 928 proximate to third end 918 and fourth end 920, respectively. First rod 902 and second rod 916 each further comprise biologically compatible sleeve 930 and 932 respectively. In at least one embodiment, sleeves 930 and 932 may have the same characteristics as described herein for sleeve 824. Sleeve 930 is removably connected to first end 904 of first rod 902 and may removably engage third end 918 of second rod 916. Sleeve 932 is removably connected to second end 906 of first rod 902 and may removably engage fourth end 920 of second rod 916.

In at least the embodiments described herein, permanent magnetic materials may be used. In at least some embodiments, the permanent magnetic materials are selected to be thin, smooth ferromagnetic bars. Saturation hysteresis loop is an important feature for these permanent magnet materials. During the process of magnetizing the sample, the magnet is subjected to a field that produces a flux density close to saturation. When the magnetizing field is reduced to zero, the induction drops back to the original value. If the magnetizing field is reversed, the magnetic poles of the thin, smooth ferromagnetic bars are reversed.

A frequently used criterion of quality of a permanent magnet is the $(BH)_{max}$ product. This is the maximum value that can be obtained by multiplying the corresponding B and H values at the point of operation on the demagnetization curve, wherein B is the magnetic flux density and H is the magnetic field strength. Here, H is directly created by the electric current, I, in the magnetic circuits. The magnetomotive force, F, is decided by the magnetic flux (BA) and the distance, D, between the attractive magnetic poles.

With a wide variation of properties available in permanent magnet materials, the following criteria may be considered in selecting the optimum material for the current application: 1) application-magnetic field requirement, 2) physical or mechanical-space factor, 3) weight, 4) stability requirements, 5) ductility requirements, 6) biocompatibility and 7) cost. Dependent on the therapeutic situation, various embodiments are envisioned which emphasize different criteria.

Ferromagnetic bars used in at least some of the embodiments may comprise many different materials dependent on the usage and properties desired. In at least one embodiment, the ferromagnetic bar may consist essentially of polymer-bonded neodymium-iron-boron (Nd—Fe—B) magnets formed by compression molding, in which magnet powders are mixed with a polymer carrier matrix, such as epoxy, which then solidifies to give shape to the magnetic material. Ferromagnetic bars used herein may also be comprised of a Heusler alloy. Heusler alloys which may be used in an exemplary embodiment, of a ferromagnetic bar, include, but are not limited to, $Fe_{80}B_{20}$, carbon coated metal particles, $Cu_2MnAl$, $Cu_2MnIn$, $Cu_2MnSn$, $Ni_2MnAl$, $Ni_2MnIn$, $Ni_2MnSn$, $Ni_2MnSb$, $Co_2MnAl$, $Co_2MnSi$, $Co_2MnGa$, $Co_2MnGe$, $Pd_2MnAl$, $Pd_2MnIn$, $Pd_2MnSn$, and $Pd_2MnSb$.

Computation of Magnetic Force

In at least some embodiments, the horizontal force, which is the force determining the circumferential size of the bar (and therefore the size of the deformed body channel), may be computed in a number of ways. Referring to FIG. 3, when only $B_x$ is considered, the stress tensor vector can be changed as:

$$P = \begin{bmatrix} \frac{|B_x|^2}{2\mu} & 0 & 0 \\ 0 & -\frac{|B_x|^2}{2\mu} & 0 \\ 0 & 0 & -\frac{|B_x|^2}{2\mu} \end{bmatrix} \begin{pmatrix} n_x \\ 0 \\ 0 \end{pmatrix} = \frac{|B_x|^2}{2\mu} \quad [1]$$

The fringe loss of magnetic flux density is assumed to be 0.5 Teslas. For example, an exemplary embodiment of a deformation device may comprise a left magnetic bar comprised of polymer-bonded Nd—Fe—B magnets and a right magnetic bar comprised of Heusler alloy or carbon-coated metal particles. When $|B_x|=0.1\times0.5=0.05$ T, the pressure on the left and right magnetic bars can be calculated as follows:

$$P = \frac{|B_x|^2}{2\mu} = \frac{0.05^2}{8\pi \times 10^{-7}} = 1.0 \text{ (KPa)} \quad [2]$$

When area=$\pi \times (10\times 10^{-3})^2 = 3.14\times 10^{-4}$ m$^2$, the maximum attractive magnetic force on the left and right magnetic bars may be calculated as follows:

$$F = P \times \text{area} = 1.0\times 10^3 \times 3.14 \times 10^{-4} = 0.314 \text{(Newton)} \quad [3]$$

It should be noted that the aforementioned equations are presented as merely one example of how such calculations may be carried out. As such, these equations are by no means meant to be limiting and additional embodiments may be carried out by other calculations as well as would be apparent to one having ordinary skill in the art after consideration of the present disclosure.

Figure 10:
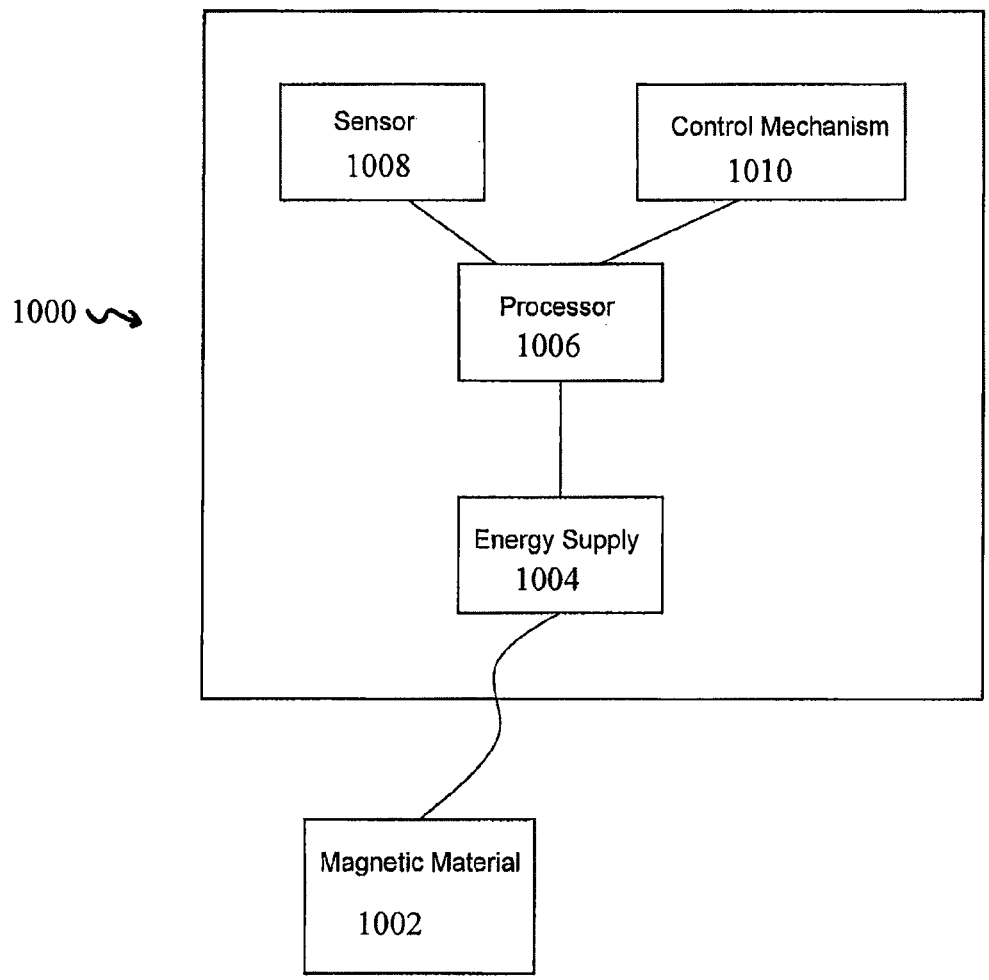
FIG. 10 shows a diagram of an embodiment of the power source, as described herein.

Referring to FIG. 10, at least one embodiment of power source 1000 is described. In at least this embodiment, power source 1000 serves to supply an electrical current to the first wire in electrical communication with a ferromagnetic bar, as described herein, collectively referred to as magnetic material 1002. Passage of electrical current through magnetic material 1002 may in at least some embodiments form an inducer. The magnitude of the magnetic force generated by the inducer depends on the material of the magnet, such as the ferromagnetic bar, and on the amount of current passed through the inducer. Increase of the level of current supplied by energy supply 1004 raises the level of magnetic force generated accordingly. Similarly, a decrease in the electric current results in a decrease in the magnetic force. Even after the electric current is turned off though, residual magnetic forces may still remain.

Power source 1000, in at least one embodiment, comprises magnetic material 1002, energy supply 1004, processor 1006, sensor 1008, and control mechanism 1010. Magnetic material 1002 is as described in at least any one of the embodiments described herein. For example, as described with respect to FIGS. 6-9, any one of the ferromagnetic bars proximate to the ends of the first or second bars may be in contact with a first wire. The first wire is additionally in communication with energy supply 1004. Energy supply 1004 may be internal or external to the body, and in at least some embodiments energy supply 1004 may comprise a battery. In at least some embodiments, energy supply 1004 may be implanted subcutaneously in the body. Additionally, in at least one embodiment, energy supply 1004 is operably connected to processor 1006.

Further, processor 1006 is operably connected to both sensor 1008 and control mechanism 1010. In at least this embodiment, processor 1006 is operable to manage the information generated by sensor 1008, and acts to implement the commands of control mechanism 1010

Sensor 1008, in at least one embodiment, serves to determine the functionality of the deformation device, and/or the characteristics of the body to which the deformation device interacts. The monitoring carried out by sensor 1008 is operable to detect a predetermined variable. In at least one embodiment, sensor 1008 may detect the deformation of the body channel. The predetermined variables detectable by sensor 1008 may include any of the flow rate of a material within the body channel, the level of pressure exerted by the first rod or second rod on the body channel, temperature, and the functional nature of the deformation device. Readings from sensor 1008 may be supplied directly to processor 1006. Further, the predetermined variables detected by sensor 1008 may be altered either through processor 1006 or by additional intervention, such as for example, mechanical intervention.

Control mechanism 1010 serves in at least one embodiment as the actuator for the deformation device. In at least some embodiments, control mechanism 1010 signals processor 1006 to activate energy supply 1004 so as to provide an electrical current to magnetic material 1002. Further, control mechanism 1010 may also serve to halt this supply of electrical current. The level of electrical current supplied by energy supply 1004 may be of a preset level. In at least one embodiment, control mechanism 1010 allows a range of electrical current to be supplied to magnetic material 1002.

Manipulation of control mechanism 1010 may be accomplished either automatically or manually. In the automatic manipulation of control mechanism 1010, processor 1006 may monitor a variable, such as time, which when reaching a preset amount may signal communication mechanism 1010 to change the level of electrical current supplied from energy supply 1004 to magnetic material 1002. Further, in at least one embodiment, processor 1006 monitors the data accumulated by sensor 1008 so as to modify the activity of control mechanism 1010 should a preset variable be reached. For example, should sensor 1008 sense that first rod 802 is exceeding a preset threshold level of pressure exertion, processor 1006 would signal control mechanism 1010 to decrease the level of electrical current supplied by energy supply 1004 to magnetic material 1002.

Manual manipulation of control mechanism 1010 may be accomplished instead of, or in addition to, automatic manipulation. In at least some embodiments, manual manipulation may be accomplished through physical interaction with control mechanism 1010 or by electrical communication with control mechanism 1010. For example, the activation level of control mechanism 1010 may be altered through the use of a remote control-type device.

In at least one embodiment, processor 1006 may record, display and/or transmit data generated by deformation device 800. Data generated by the deformation device may include measurements taken by sensor 1008, instructions by control mechanism 1010, levels of current supplied to magnetic material 1002. Processor 1006 may store this data in a capacity to be retrieved or displayed at a later time. Display of the data by the processor may be in form comprehendible to an individual. Further, processor 1006 may transmit the data generated to a secondary processor for additional uses.

Body channels, such as those illustrated in FIGS. 5A-C, may comprise many different structures within the body. In at least one embodiment, the body channel comprises a vessel within a body which may serve to supply, or allow the passage therethrough of, a liquid or solid. For example, a body channel may include any sphincter, such as the upper esophageal sphincter, the lower esophageal (or Cardia) sphincter, the pyloric sphincter, the Illeocecal sphincter, the sphincter of Oddi, the urethral sphincter, the internal anal sphincter, and external anal sphincter. Additionally, the vessels which connect to, or supply, these sphincters will be considered body channels.

Methods of use of at least one embodiment of the deformation device are described herein. In at least one embodiment, a deformation device comprising a first rod, a first wire, and a power source is introduced proximate to a body channel. In this embodiment, the first rod has a first end and a second end, a first ferromagnetic bar proximate to the first end and a second ferromagnetic bar proximate to the second end. Additionally, a portion of the first wire is in contact with the first rod and is electrically coupled with the power source. Following the introduction of the deformation device, the first rod, or optionally a plurality of rods, is then positioned so as to substantially encircle a body channel. After positioning, the first rod is secured so as to be substantially immobile. Securing the first rod may be accomplished through any known means to a person skilled in the art. For example, the first rod may be secured through suture, biocompatible adhesives, or bindings. Following securing of the first rod, an electrical current to the desired level is supplied to the first wire to form an inductor. Additionally, application of the electrical current in some embodiments may cause a constriction of a body channel by the first, or plurality of, rods, Optionally, the implantation of the deformation device may include the introduction of a sleeve material so as to protect a portion of the first rod from contact with an external structure. The body channels which may be deformed through this method include, but are not limited to the upper esophageal sphincter, lower esophageal (or cardia) sphincter, pyloric sphincter, Illeocecal sphincter, sphincter of Oddi, urethral sphincter, internal anal sphincter, and external anal sphincter. Additionally, body channels connected to the above-mentioned sphincters maybe acted on as well in some embodiments.

The method of deformation of a body channel, according to one exemplary embodiment, may act to constrict a body channel for the treatment of an abnormal, or undesired, condition. According to an exemplary embodiment of a method disclosed herein, for the treatment of gastroesophageal reflux disease, the embodiment includes the steps of introducing deformation device 800 proximal to the lower esophageal sphincter. Deformation device 800, in this embodiment, comprises first rod 802 having first end 804 and second end 806. First rod 802 further comprises first portion 808 and second portion 810, wherein first portion 808 is comprised of a material sufficiently rigid as to exert a force upon the lower esophageal sphincter, and wherein second portion 810 is comprised of a material sufficiently malleable as to distribute the force of first portion 808 upon the lower esophageal sphincter, so as not to inflict damage on the sphincter or surrounding structures. First rod 802 further comprises ferromagnetic bars 812 and 814 proximate to first end 804 and second end 806, respectively. Additionally, first rod 802 further comprises two additional ferromagnetic bars 816 and 818 located between ferromagnetic bars 812 and 814, and joint member 822 located between ferromagnetic bars 816 and 818. Ferromagnetic bars 812, 814, 816, and 818 are in contact with a wire electrically coupled to power supply 820. Power supply 820 comprises energy source 1004, processor 1006, sensor 1008, and control mechanism 1010. Following introduction of deformation device 800, deformation device 800 is positioned as to substantially encircle the lower esophageal sphincter. Deformation device 800 may then be secured at a point proximal to the lower esophageal sphincter through use of sutures. Electrical current from energy source 1004 is then applied to wire 824, and adjusted either manually or automatically, as appropriate, to deform the lower esophageal sphincter. Joint member 822 allows for an increased capacity for the flexure of first rod 802. Sensor 1008 detects the flow of materials within the lower esophageal sphincter, and deformation of the lower esophageal sphincter to preset limits. Detection of values outsides the preset limits by sensor 1008 triggers control mechanism 1010 to cause processor 1006 to increase or decrease the current supplied by energy supply 1004 as appropriate.

Additional embodiments of the method may affect additional body channels such as the urinary sphincter to control urinary incontinence, and the interior or exterior anal sphincter for control of fecal incontinence. Deformation of the urinary sphincter or surrounding vessels by an embodiment of the deformation device may provide control of urinary output, and thus relief from urinary incontinence. Control of urinary output, may in an embodiment be performed manually by altering the electrical current supplied to the deformation device. In an embodiment, this alteration in current would serve to compress or release the urinary sphincter as needed. Additionally, deformation of the interior or exterior anal sphincter may be used to control fecal incontinence as was described above for the control of urinary incontinence.

For deformation of a body channel, an embodiment of a deformation device may interact with channels operably connected to the body channel in question to accomplish the same desired effect. For example, deformation of the esophagus may effect any area of the esophagus as well as the lower or upper esophageal sphincter. Additionally, deformation of the neck of the bladder may affect any area of the urinary passage which comprises the urethra as well as the urinary sphincter. Further, deformation of the rectal passage may affect any area of the rectum as well as the internal anal sphincter and external anal sphincter.

While various embodiments of devices, systems, and methods for deforming a body channel have been described in considerable detail herein, the embodiments are merely offered by way of non-limiting examples of the invention described herein. Many variations and modifications of the embodiments described herein will be apparent to one of ordinary skill in the art in light of the this disclosure. It will therefore be understood by those skilled in the art that various changes and modifications may be made, and equivalents may be substituted for elements thereof, without departing from the scope of the invention. Indeed, this disclosure is not intended to be exhaustive or to limit the scope of the invention. The scope of the invention is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present invention.

It is therefore intended that the invention will include, and this description and the appended claims will encompass, all modifications and changes apparent to those of ordinary skill in the art based on this disclosure.

We claim:

1. A device for deforming a mammalian body channel, the device comprising:
 a first rod, comprising:
  a first end,
  a second end magnetically attracted to the first end,
  wherein a first portion of the first rod extends from the first end to the second end, the first portion sufficiently rigid so as to exert a force upon a body channel to deform the body channel when positioned thereon,
  a second portion substantially surrounding the first portion, the second portion comprising a malleable portion sufficient to distribute the force exerted upon the body channel by the first portion;

a first ferromagnetic bar proximate to the first end and a second ferromagnetic bar proximate to the second end;

a first wire, wherein at least a portion of the first wire is adjacent to at least one of the first ferromagnetic bar and the second ferromagnetic bar; and a power source, the power source electrically coupled to the first wire;

wherein the power source is operable to provide an electric current through the first wire to at least one of the first ferromagnetic bar and the second ferromagnetic bar; and wherein at least one of the first ferromagnetic bar and the second ferromagnetic bar generates a magnetic field when the first wire is energized; and wherein the power source further comprises a control mechanism and a processor operable to process data.

2. The device of claim 1, wherein the first end and second end exhibit a transient magnetic force; and wherein the first rod is capable of deforming a body channel through the transient magnetic force.

3. The device of claim 1, wherein the magnetic field generates a transient magnetic force between the first ferromagnetic bar and the second ferromagnetic bar.

4. The device of claim 1, wherein the power source comprises a battery.

5. The device of claim 1, wherein the control mechanism is capable of manual adjustment.

6. The device of claim 1, further comprising a sensor in communication with the power source.

7. The device of claim 6, wherein the sensor is operable to detect a predetermined variable, and wherein the control mechanism is adjusted automatically through use of the processor by the sensor upon reaching a preset value for the predetermined variable.

8. The device of claim 6, wherein the sensor is operable to detect deformation of the body channel due to a change in pressure or force exerted on the body channel.

9. The device of claim 6, wherein the sensor is operable to detect the flow of a material within the body channel.

10. The device of claim 6, wherein the sensor is operable to detect a level of pressure exerted by the first rod on the body channel.

11. The device of claim 6, wherein the sensor is operable to detect temperature.

12. The device of claim 1, wherein the first rod further comprises a joint member, the joint member partitioning the first rod into a proximal segment and a distal segment, wherein the joint member allows flexure of the first rod.

13. The device of claim 12, further comprising a sleeve at least partially sheathing a portion of the first rod, wherein the sleeve substantially shields exterior surfaces from contact with the electric current.

14. The device of claim 13, wherein the sleeve is comprised of a material selected from the group consisting of silicone, polytetrafluoroethylene, and a biological material.

15. The device of claim 13, wherein the sleeve is comprised of a material selected from the group consisting of small intestinal submucosal material and pericardial tissue.

16. The device of claim 13, wherein the sleeve is comprised of a biological material.

17. The device of claim 1, wherein the device is configured to be secured proximate to the body channel by a securing mechanism.

18. The device of claim 1, wherein the first rod further comprises at least one additional ferromagnetic bar located between the first ferromagnetic bar and the second ferromagnetic bar, wherein the at least one additional ferromagnetic bar is configured to increase a potential deformative force of the first rod.

19. The device of claim 1, wherein at least one of the first ferromagnetic bar and the second ferromagnetic bar comprises a material selected from the group consisting of neodymium, iron, boron, a Heusler alloy, $Cu_2MnAl$, $Cu_2MnIn$, $Cu_2MnSn$, $Ni_2MnAl$, $Ni_2MnIn$, $Ni_2MnSn$, $Ni_2MnSb$, $Co_2MnAl$, $Co_2MnSi$, $Co_2MnGa$, $Co_2MnGe$, $Pd_2MnAl$, $Pd_2MnIn$, $Pd_2MnSn$, $Pd_2MnSb$, and carbon-coated metal particles.

20. The device of claim 1, wherein the body channel is selected from a group consisting of an upper esophageal sphincter, a lower esophageal (or cardia) sphincter, a pyloric sphincter, an Illeocecal sphincter, a sphincter of Oddi, a urethral sphincter, an internal anal sphincter, and an external anal sphincter.

21. The device of claim 1, wherein the body channel is an esophagus, and wherein the device is configured to exert the force which is sufficient to deform the body channel to deform the esophagus to provide gastroesophageal reflux disease relief.

22. The device of claim 1, wherein the body channel is a neck of a bladder, and wherein the device is configured to exert the force which is sufficient to deform the body channel to deform the neck of the bladder to provide urinary incontinence relief.

23. The device of claim 1, wherein the body channel is a rectal passage, and wherein the device is configured to exert the force which is sufficient to deform the body channel to deform the rectal passage to provide fecal incontinence relief.

24. The device of claim 1, further comprising:

a second rod having a third end, a fourth end, a third portion extending from the third end to the fourth end, and a fourth portion substantially surrounding the third portion;

wherein the first end and the fourth end are operable to magnetically attract one another, and the second end and the third end are operable to magnetically attract one another;

wherein at least two of the first end, the second end, the third end and the fourth end exhibit a transient magnetic force; and wherein the first rod and second rod in conjunction are capable of deforming a body channel through the transient magnetic force.

25. The device of claim 24, wherein the third portion is sufficiently rigid so as to exert a force upon a body channel; and wherein the fourth portion comprises a malleable portion sufficient to distribute the force of the third portion exerted upon the body channel.

26. A system for the deformation of a mammalian body channel, the system comprising:

a first rod, comprising:

a first end, a second end magnetically attracted to the first end, wherein a first portion of the first rod extends from the first end to the second end, the first portion sufficiently rigid so as to exert a force upon a body channel to deform the body channel when positioned thereon, and a second portion substantially surrounding the first portion, the second portion comprising a malleable portion sufficient to distribute the force exerted upon the body channel by the first portion;

a first wire having a proximal wire end and a distal wire end, wherein at least a portion of the first wire is adjacent to a portion of the first rod;

a power source operably connected to the first wire, the power source operable to provide an electric current to the first wire;

a second rod having a third end, a fourth end, a first ferromagnetic bar proximate to the third end, and a second ferromagnetic bar proximate to the fourth end; and a second wire having a proximal second wire end and a distal second wire end, a portion of the second wire coiled around a portion of the second rod;

wherein the power source is further operably connected to the second wire, the power source operable to provide an electric current to the second wire;

wherein deliverance of an electric current from the power source to the first wire and the second wire forms an inductor; and wherein the first rod and the second rod are operable for magnetic attraction to each other.

27. The system of claim 26, wherein the first rod further comprises a joint member, the joint member partitioning the first rod into a proximal segment and a distal segment, wherein the joint member allows flexure of the first rod.

28. A method of deformation of a mammalian body channel, the method comprising the steps of:

positioning a deformation device substantially around a mammalian body channel, the deformation device comprising i) a first rod having a first end, ii) a second end magnetically attracted to the first end, wherein a first portion of the first rod extends from the first end to the second end, the first portion sufficiently rigid so as to exert a force upon a body channel to deform the body channel when positioned thereon, iii) a first ferromagnetic bar proximate to the first end, iv) a second ferromagnetic bar proximate to the second end, and v) a second portion substantially surrounding the first portion, the second portion comprising a malleable portion sufficient to distribute the force exerted upon the body channel by the first portion, wherein the deformation device is operably coupled to a first wire, wherein at least a portion of the first wire is adjacent to at least one of the first ferromagnetic bar and the second ferromagnetic bar, wherein the first wire is operably connected to a power source, wherein the power source is operable to provide an electric current through the first wire to at least one of the first ferromagnetic bar and the second ferromagnetic bar, wherein at least one of the first ferromagnetic bar and the second ferromagnetic bar generates a magnetic field when the first wire is energized, and wherein the power source further comprises a control mechanism and a processor operable to process data;

securing the deformation device at a point proximate to the body channel; and deforming the body channel by introducing an electrical current from the power source to the first wire to form an inductor.

29. The method of claim 28, wherein the body channel is selected from a group consisting of a upper esophageal sphincter, a lower esophageal (or cardia) sphincter, a pyloric sphincter, an Illeocecal sphincter, a sphincter of Oddi, a urethral sphincter, an internal anal sphincter, and an external anal sphincter.

30. The method of claim 28, wherein the body channel is an esophagus, and wherein the step of deforming the body channel constricts the esophagus to provide gastroesophageal reflux disease relief.

31. The method of claim 28, wherein the body channel is a neck of a bladder, and wherein the step of deforming the body channel constricts the neck of a bladder to provide urinary incontinence relief.

32. The method of claim 28, wherein the body channel is a rectal passage, and wherein the step of deforming the body channel constricts the rectal passage to provide fecal incontinence relief.

* * * * *